United States Patent [19]

Poffenbarger

[11] Patent Number: 4,579,103
[45] Date of Patent: Apr. 1, 1986

[54] FOOT WARMING DEVICE

[76] Inventor: Perry S. Poffenbarger, 1808 Loudon Heights Rd., Charleston, W. Va. 25314

[21] Appl. No.: 656,500

[22] Filed: Oct. 1, 1984

[51] Int. Cl.$^4$ .............................................. A61F 7/00
[52] U.S. Cl. .................................. 126/204; 126/207; 126/206
[58] Field of Search ............... 126/206, 207, 208, 205, 126/204, 246, 263; 237/28, 30, 31, 43

[56] References Cited

U.S. PATENT DOCUMENTS

| 180,022 | 7/1876 | Grandjean et al. | 126/206 |
| 382,158 | 5/1888 | Henn | 126/206 |
| 595,519 | 12/1897 | Berchem | 126/204 |
| 750,060 | 1/1904 | Petty | 126/204 |

FOREIGN PATENT DOCUMENTS

| 285089 | of 1889 | France | 126/207 |
| 467209 | 3/1914 | France | 126/204 |
| 19026 | of 1889 | United Kingdom | 126/206 |

Primary Examiner—Randall L. Green
Attorney, Agent, or Firm—Cushman, Darby & Cushman

[57] ABSTRACT

A device to removably hold a solid fuel heating module includes a body member defining an open ended chamber and generally U-shaped channels in each of an opposing pair of side walls. The elongated channels are sized and configured to slidably receive a respective side edge of the heating module when the heat module is inserted in a rectilinear direction between the opposing side walls. A space is defined in a top wall in communication with the chamber so as to be in registry with the heating module and guard members bridge the space to prevent the user's foot from directly contacting the heating module contained in the chamber. A chimney defined in the body permits cool air to flow from a direction from the rear wall towards the chamber, be heated by the heat module and then transferred to the user's foot by virtue of the space defined in the top wall.

3 Claims, 4 Drawing Figures

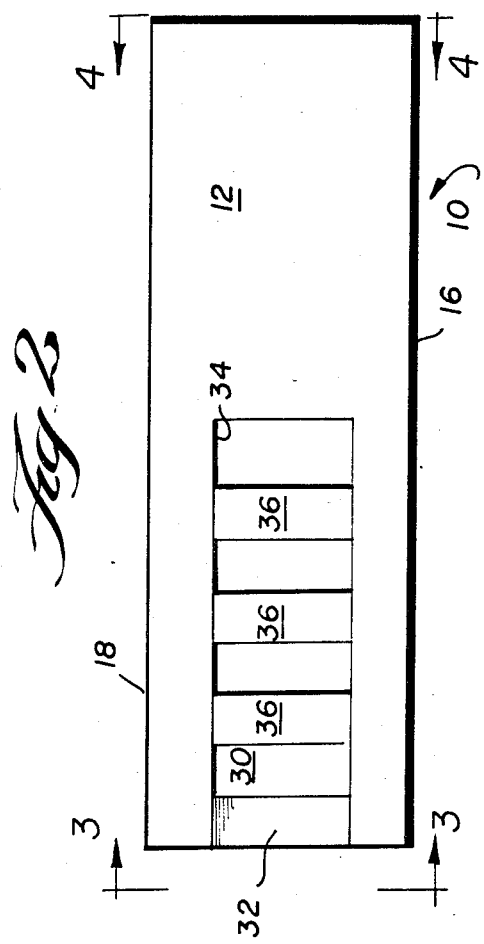
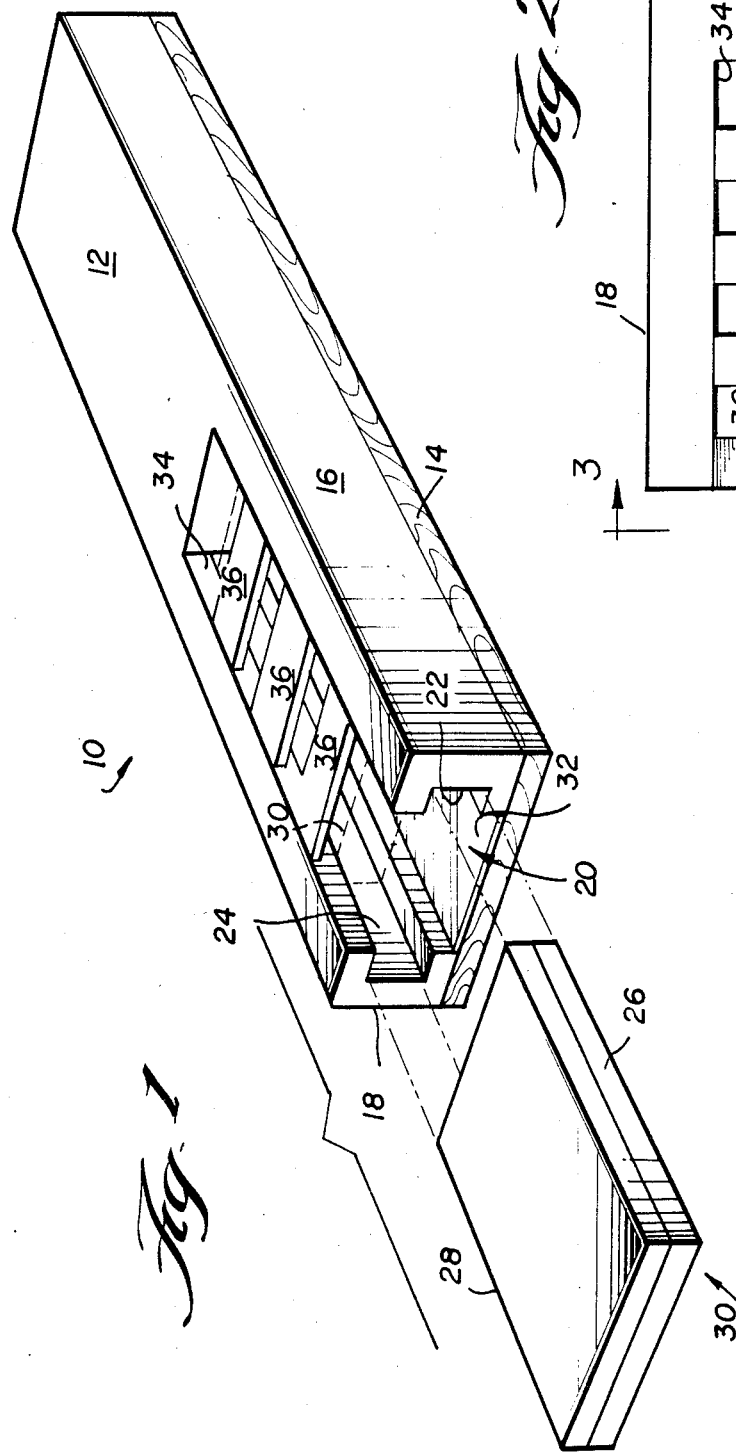
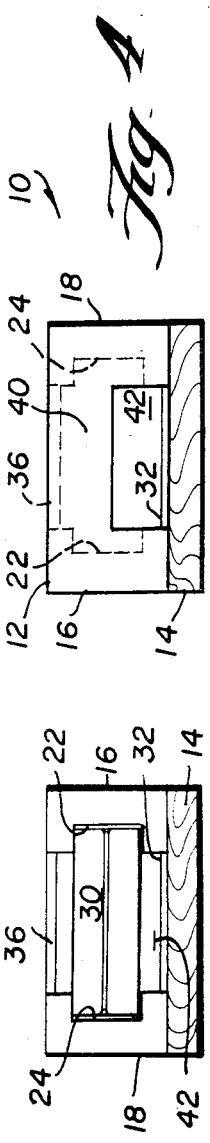
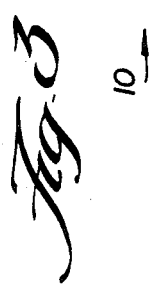

FOOT WARMING DEVICE

FIELD OF INVENTION

The present relates to devices having a heat-generating fuel module and used so as to warm a person's foot.

BACKGROUND OF THE INVENTION

Foot warming devices, in and of themselves, are not new. For example, U.S. Pat. Nos. 595,519 and 13,859 disclose box structure having a removable lid so that access can be gained to the container cavity in which a fuel module is placed. U.S. Pat. No. 3,585,736 discloses a shoe having an integral sole in which a chamber is defined to house a fuel module. U.S. Pat. No. 4,094,080 discloses that fabric sections can be stitched together so as to form plural pockets overlying the toe, instep and vamp portions of a boot or shoe such that flameless heaters can be disposed within each pocket to provide warming functions.

SUMMARY OF THE PRESENT INVENTION

In accordance with the present invention, a housing member is provided and sized so as to support a person's foot placed thereon. The housing includes a heel end and a toe end adapted to being respectively oriented so as to be in registry with the heel and toes of a person's foot. A chamber defined in the housing member at the toe end removably accepts a solid-fuel heating module therein by means of opposing longitudinal channels defined in the side walls of the housing. The heating module can thus be slidably received in the chamber due to the coupling of respective side edges of the heating module with the U-shaped channels.

A space preferably defined in a top wall of the housing member so as to be in registry with the heating module. Thus, when a person places his foot in registry with the housing, the heating element will provide sufficient warmth due to the transfer of heat by means of convection through the defined space in the top wall of the housing. Guard members bridging the space and disposed superjacent the heating module when the latter is contained in the chamber are provided so as to prevent the user's foot from directly contacting the heating module to thereby promote safe use of the present invention.

These as well as other objects and advantages of the present invention will become more clear to the reader after careful consideration is given to the detailed description of the preferred exemplary embodiment thereof which follows.

BRIEF DESCRIPTION OF THE ACCOMPANYING DRAWINGS

Reference will be hereinafter made to the accompanying drawings wherein like reference numerals throughout the various figures denote like structural elements and wherein:

FIG. 1 is a perspective view of the foot warming device of the present invention depicting the solid fuel heat module in a removed relationship therewith;

FIG. 2 is a top plan view of the device depicted in FIG. 1;

FIG. 3 is a toe end elevational view of the device taken alone line 3—3 in FIG. 2; and FIG. 4 is a heel end elevational view taken along line 4—4 in FIG. 2.

DETAILED DESCRIPTION OF THE PREFERRED EXEMPLARY EMBODIMENT

Referring to the accompanying drawings, it can be seen that the device of the present invention generally includes a body 10 having top and bottom walls 12, 14, respectively, and a pair of opposing side walls 16, 18 so as to define an inner cavity 20 at the front or toe end portion of body 10. Each side wall 16, 18 defines a respective U-shaped channel 22, 24 in opposing relationship with one another and is sized and configured so as to accept a respective portion of sides 26, 28 of solid fuel heating module 30. Solid fuel heating module 30 is, in and of itself, well known and can be, for example, a solid fuel heating module as disclosed in U.S. Pat. No. 3,547,100 to Usui, the entire disclosure of which is expressly incorporated hereinto by reference. A heat-reflective shield 32 of, e.g., metal, bakelite or the like is fixed to the bottom wall 14 in the area of cavity 20 so as to radiate heat upwardly through opening 34 formed in upper wall 12.

Plural guard members 36 bridge the lateral edges of opening 34 so as to prevent a user's foot from coming into direct contact with the heat module 30 when disposed in cavity 20 (e.g. as shown in dashed line in FIG. 1).

The back wall 40 is preferably vertically disposed so that the forward edge of a user's heel portion of the shoe can be abutted against surface 40 to maintain the user's foot position on the body 12. Furthermore, rear wall 40 defines a chimney 42 with the bottom wall 14 and side walls 16, 18 which communicates with cavity 20. Moreover, since channels 22, 24 are vertically displaced above bottom wall 14, heating module 30 will be upwardly separated from bottom wall 14. Thus, when heat module 30 is positioned in cavity 20 (as shown in dotted line in FIG. 1), chimney 42 will communicate with cavity 20 such that cool air will be induced to flow into chimney 42 in a direction from rear wall 40 towards cavity 20. Such cool air will thus be heated by heat module 30 and the warm air will then pass to the user's foot via opening 34.

To use the device in accordance with the present invention, one lights a solid fuel member (not shown) contained in heat module 30 and then slides the edges 26, 28 into contact with the U-shaped channels 22, 24, respectively defined in side walls 16, 18. The user linearly slides module 30 into its final position as shown in dashed line in FIG. 1. The user then positions his foot such that the heel portion of his shoe will be abutted against end wall 40 while the sole portion of the user's shoe will rest upon top wall 12 such that the toe area is in registry with opening 34. The cool air supplied to cavity 20 by virtue of chimney 42 will thus be heated and transferred to the user's foot by way of opening 34.

Although the present invention has been described in what is presently conceived to be the most preferred embodiment thereof, those in this ar may recognize that many modifications may be made hereof, which modifications shall be accorded the broadest scope of the appended claims so as to encompass all equivalent structures, assemblies and devices.

What is claimed is:

1. A device for warming a person's foot comprising in combination:

a housing member sized to support a person's foot placed thereon, said housing member having a heel end adapted to being oriented in registry with the heel of a person's foot and a toe end adapted to be oriented to be in registry with the toes of a person's foot, said housing member including a top wall and a bottom wall separated vertically by means of a pair of opposing side walls;

a chamber formed by said housing member and having a pair of openings respectively formed at said toe and heel ends, said chamber extending through said housing member between said pair of openings respectively formed through said housing member between said pair of openings respectively formed at said toe and heel ends;

an opposing pair of channel members formed in and at least along a forward longitudinal portion of said pair of side walls to thereby define an opposing pair of longitudinal U-shaped channels each of which extends along a respective said side wall and is in communication with said chamber, said U-shaped channels being vertically separated above said bottom wall by a predetermined dimension to facilitate air flow through said chamber;

a solid fuel heating module disposed in said chamber, said module including at least upper and lower module sections coupled to one another and a solid combustible fuel material placed therebetween, said upper and lower module sections thereby establishing opposing sides of said module which are slidably and removably coupled in a respective one of said U-shaped channels, said U-shaped channels thereby enveloping said module sides and adjacent portions of said upper and lower module sections so that said heating module is removably insertable into and from said chamber directly through said opening formed at said toe end of said housing member; and an aperture defined by a forward portion of said top wall of said housing member thereby permitting heat from said heating module to be upwardly transferred to a person's foot; wherein said heating module is located in subjacent registry with said aperture and partially obstructs said opening of said chamber at said toe end and is vertically separated above said bottom wall of housing member by means of said U-shaped channels to thereby permit air to flow into said chamber through said pair of openings and to be heated below said heat module by virtue of its vertical separation above said bottom, wherein said heated air is then upwardly transferred to a person's foot resting upon said top wall by virute of said aperture defined thereby.

2. A device as in claim 1 further comprising guard means bridging said aperture for preventing a user's foot from contacting said heating module in said chamber.

3. A device as in claim 5 further comprising:

heat reflector means for reflecting heat generated by said fuel upwardly, said heat reflector means being located below said fuel module;

wherein the combination of said air flow and said reflected heat effectively allows the bottom-most portion of said housing means to stay cool.

* * * * *